(12) United States Patent
Li

(10) Patent No.: US 7,023,563 B2
(45) Date of Patent: Apr. 4, 2006

(54) INTERFEROMETRIC OPTICAL IMAGING AND STORAGE DEVICES

(76) Inventor: Chian Chiu Li, 1034 W. Iowa Ave. #3, Sunnyvale, CA (US) 94086

( * ) Notice: Subject to any disclaimer, the term of this patent is extended or adjusted under 35 U.S.C. 154(b) by 310 days.

(21) Appl. No.: 10/367,510

(22) Filed: Feb. 14, 2003

(65) Prior Publication Data

US 2004/0160611 A1    Aug. 19, 2004

(51) Int. Cl.
*G01B 9/02* (2006.01)
(52) U.S. Cl. ..................................... 356/521
(58) Field of Classification Search ............... 356/497, 356/499, 511, 512, 513, 514, 521
See application file for complete search history.

(56) References Cited

U.S. PATENT DOCUMENTS

| 4,639,139 A | 1/1987 | Wyant et al. |
| 4,732,483 A | 3/1988 | Biegen |
| 4,893,931 A * | 1/1990 | Lefevre et al. ............. 356/479 |
| 5,131,748 A * | 7/1992 | Monchalin et al. ......... 356/486 |
| 5,321,501 A | 6/1994 | Swanson et al. |
| 5,333,045 A * | 7/1994 | Gusmeroli et al. ......... 356/479 |
| 5,841,583 A | 11/1998 | Bhagavatula |
| 5,883,875 A | 3/1999 | Coufal et al. |
| 6,072,765 A | 6/2000 | Rolland et al. |

OTHER PUBLICATIONS

D. Huang, E. A. Swanson, C. P. Lin, J. S. Schuman, W. G Stinson, W Chang, M. R. Hee, T. Flotte, K. Gregory, C. A. Puliafito, J. G. Fujimoto, "Optical Coherence Tomography," Science, 1991, vol. 254, pp. 1178-1181.
K. Creath and A. Morales, Chapter 17 "Contact and Noncontact Profilers," Book title: "Optical Shop Testing," pp. 687-714, Second Edition, Edited by Daniel Malacara, 1992, John Wiley & Sons, Inc.
J. M. Schmitt, "Optical Coherence Tomography (OCT): A Review," IEEE Journal of Selected Topics in Quantum Electronics, Jul./Aug. 1999, vol. 5, No. 4, pp. 1205-1215.

* cited by examiner

*Primary Examiner*—Gregory J. Toatley, Jr.
*Assistant Examiner*—Michael A. Lyons

(57) ABSTRACT

An interferometric optical device divides a beam into two beam portions by wavefront division and produces a tunable phase difference between them. Next a sample and a reference reflector reflect the beam portions respectively. Then interference between the reflected beam portions is used for topography, tomography, and readout of multi-layer optical data storage media.

20 Claims, 7 Drawing Sheets

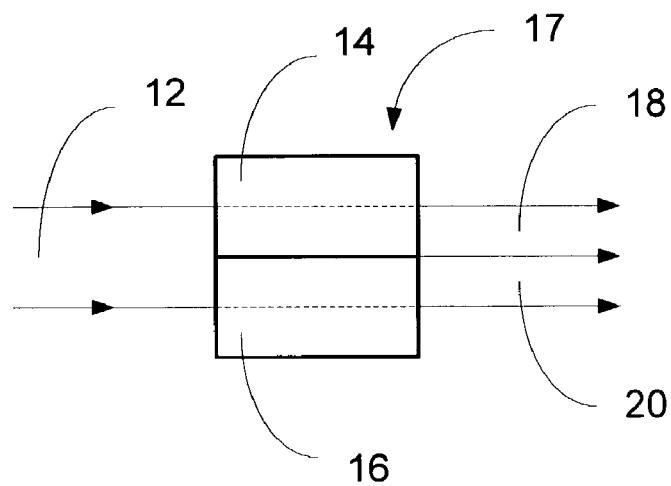
FIG. 1
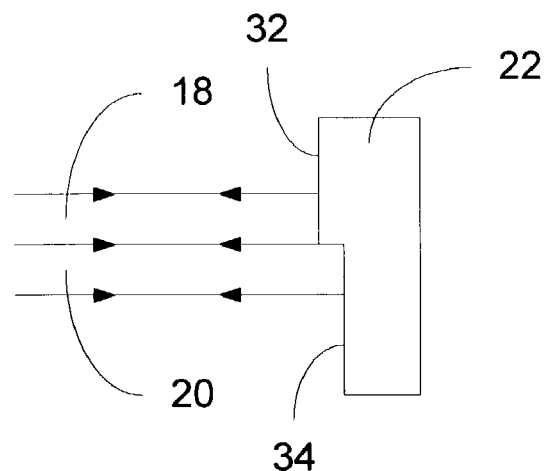
FIG. 2-A
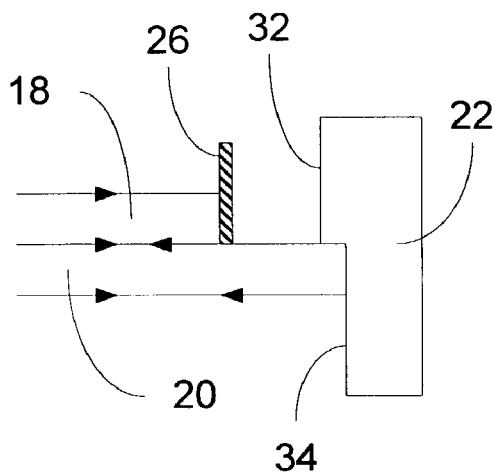
FIG. 2-B

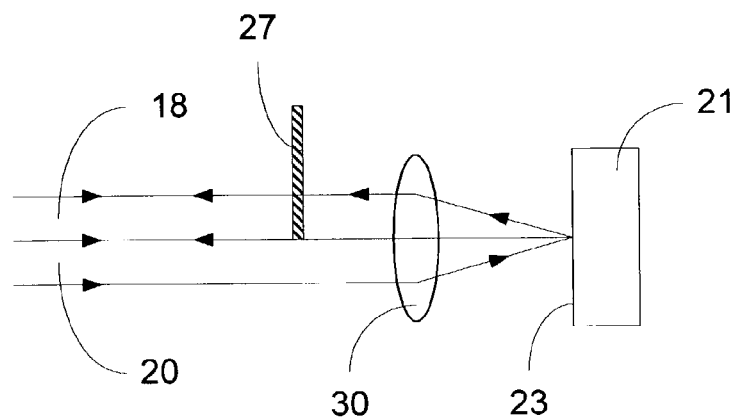
FIG. 2-C
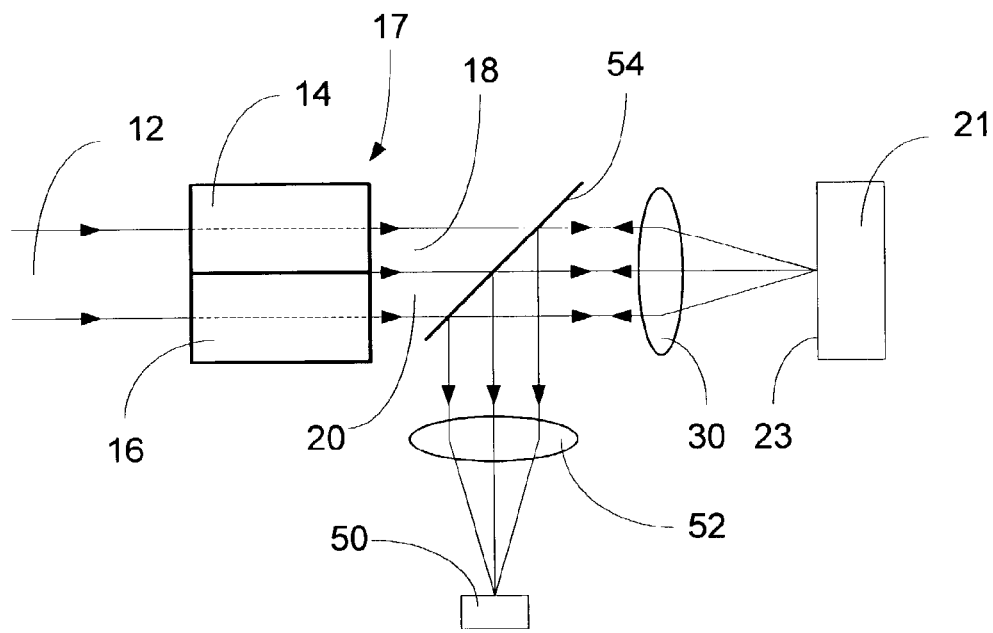
FIG. 3

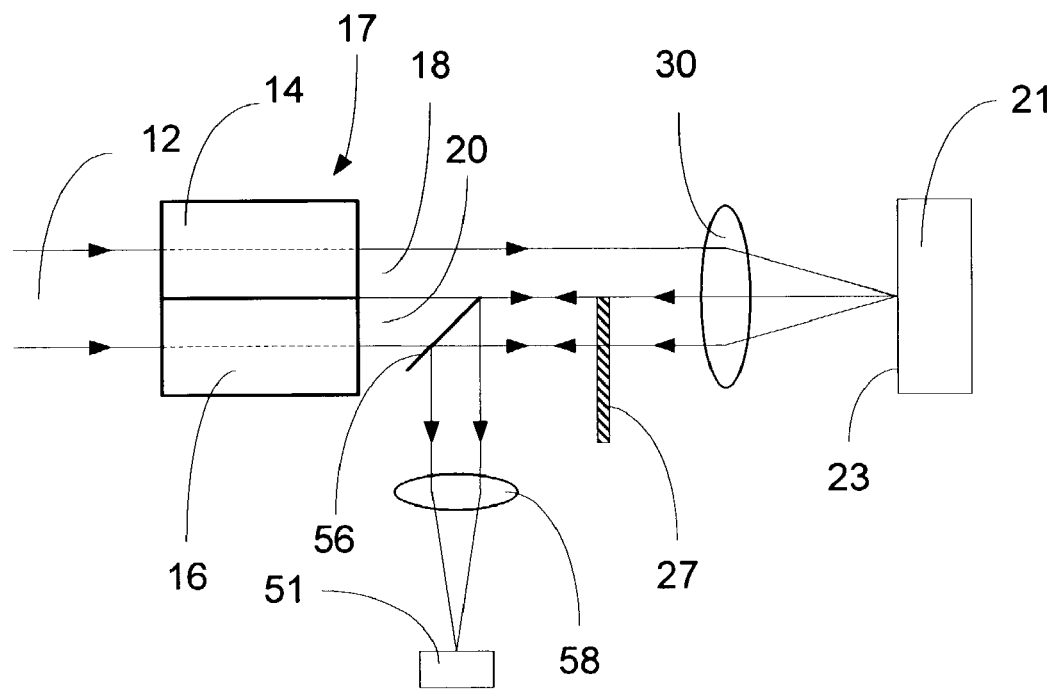
FIG. 4
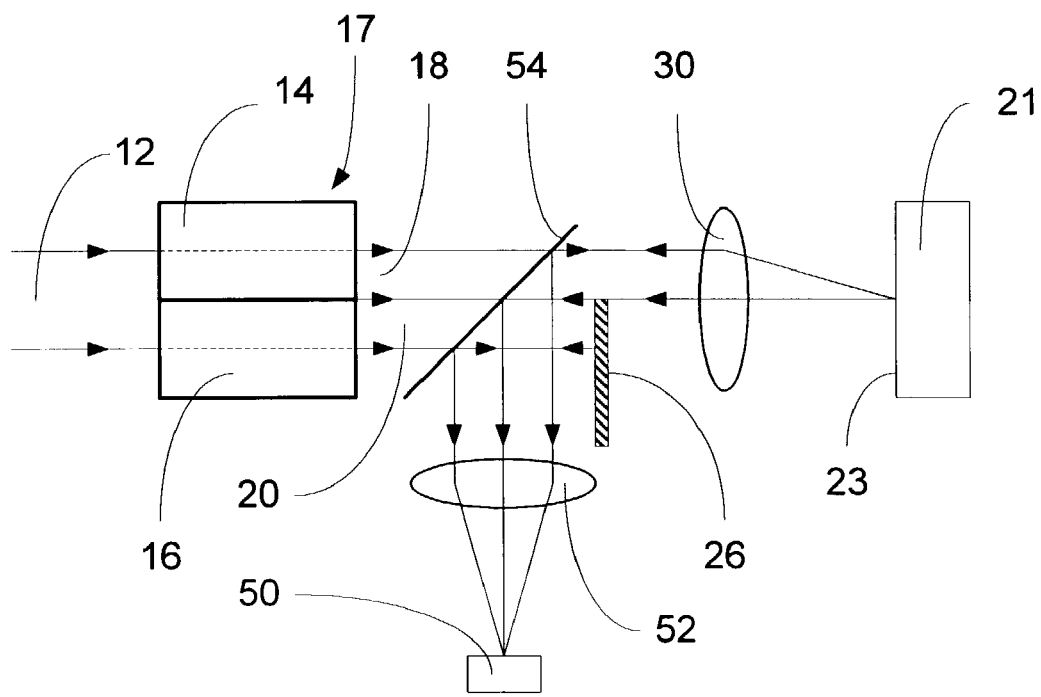
FIG. 5-A

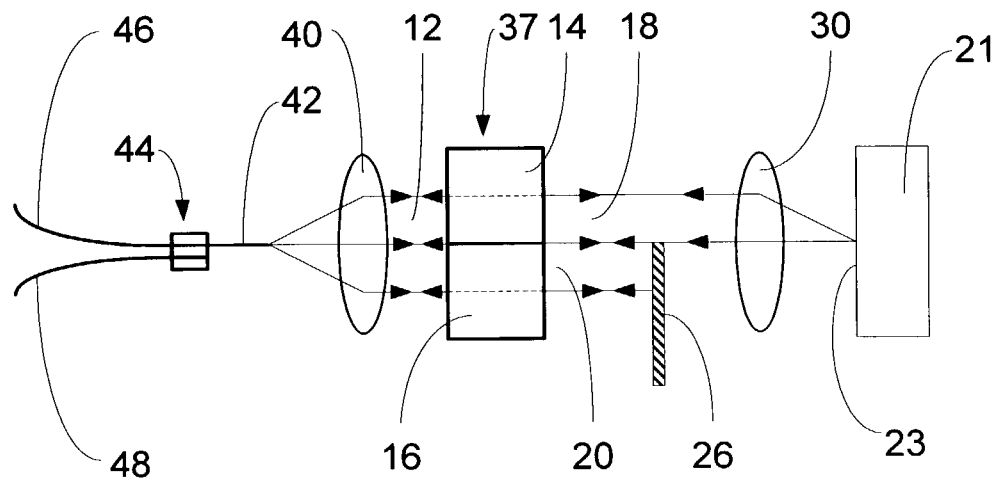
FIG. 5-B
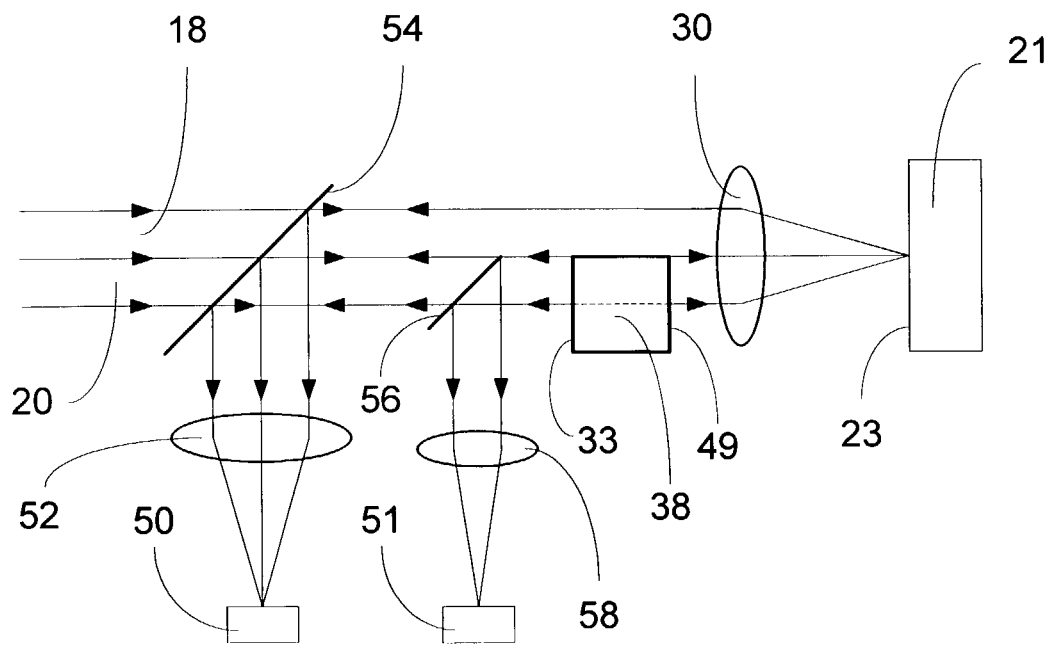
FIG. 6

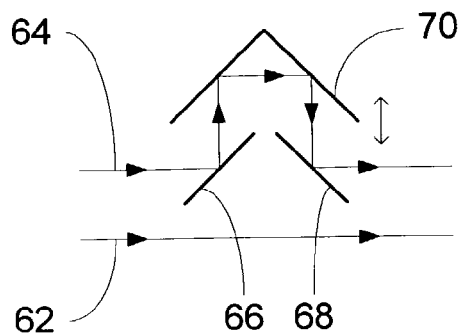
FIG. 7-A
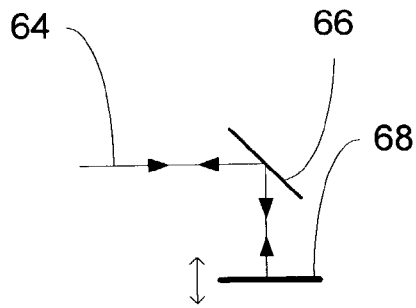
FIG. 7-B
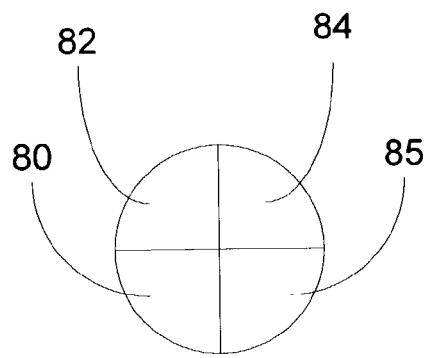
FIG. 7-C
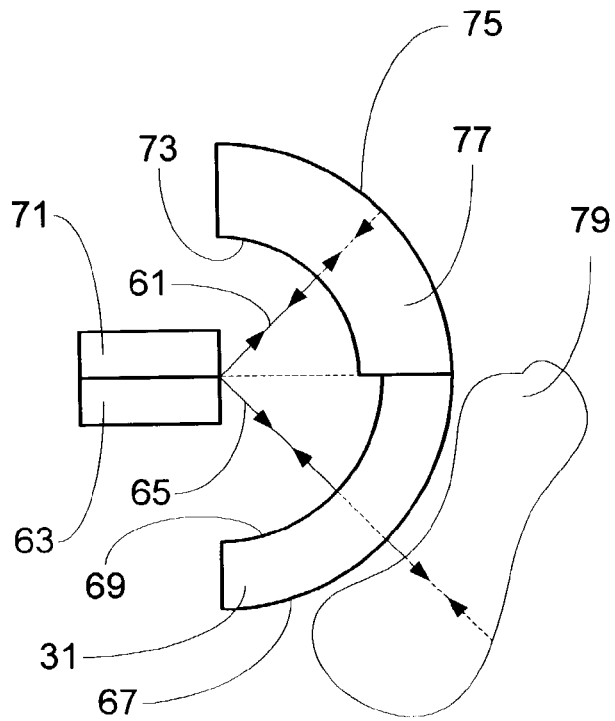
FIG. 8-A

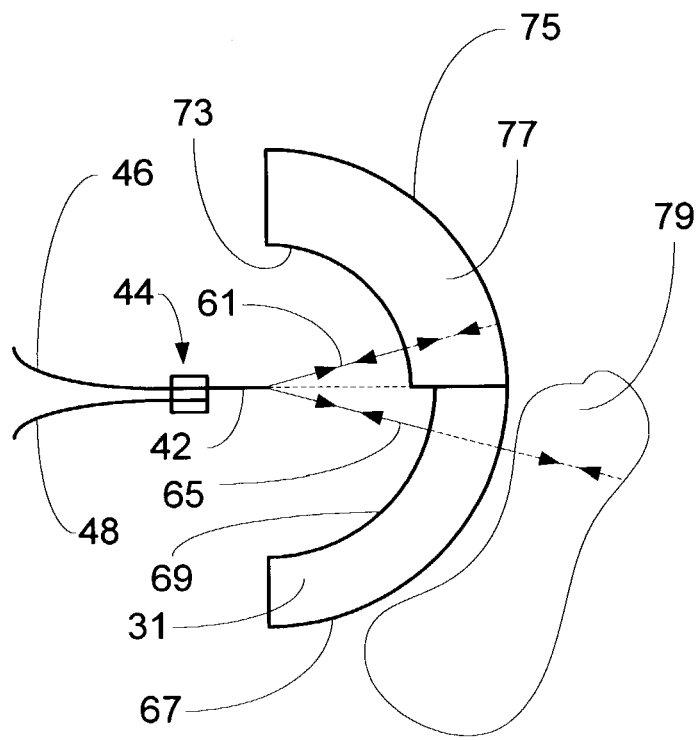
FIG. 8-B
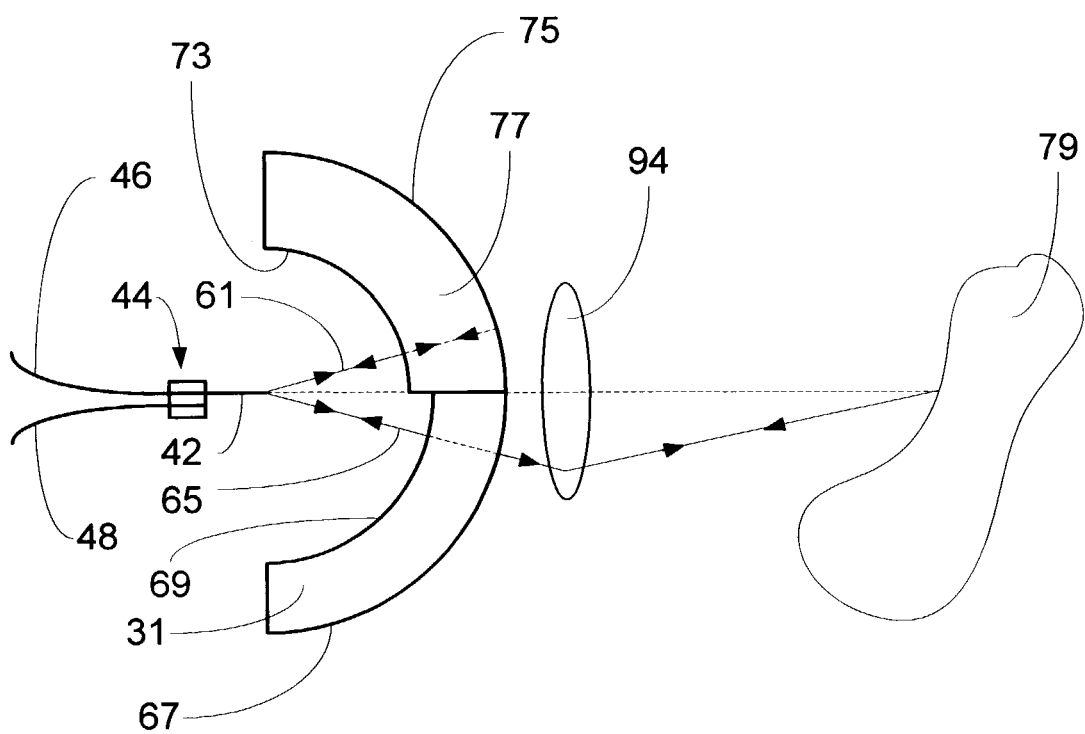
FIG. 8-C

INTERFEROMETRIC OPTICAL IMAGING AND STORAGE DEVICES

FEDERALLY SPONSORED RESEARCH

Not applicable

SEQUENCE LISTING OR PROGRAM

Not applicable

BACKGROUND

1. Field of Invention

This invention is related to interferometric optical devices of wavefront division, particularly to interferometric optical devices used in topography, biomedical tomography, and optical data storage technologies.

2. Description of Prior Art

An interferometric optical profiler is a device which uses optical interference to measure topography of a sample surface. Topography measurements are often required in semiconductor, data storage, and fiberoptic telecommunication industries. For example, inspection of a silicon wafer includes surface measurements in semiconductor manufacturing. There are two major types of interferometric optical profilers: imaging and scanning types. Both types rely on interference of amplitude division.

An imaging type profiler produces an optical image of a surface area. It is usually based on Michelson, Mirau, Linnik, or Fizeau interferometers, which use a beam splitter to split a beam from a light source into two beams by amplitude division. The two beams travel along separate paths and are reflected by a reference surface and a sample surface, respectively. The reflected beams are then recombined by the beam splitter to construct an interference pattern. The interference pattern depends upon two factors: optical path length difference between the two paths and the sample's surface profile. The measurement is fast, but is sensitive to vibration since vibration changes the optical path length difference.

A scanning type profiler scans a surface to collect topography data. It is usually based on a concentric-beam interferometer or a common-path polarization interferometer. Although a scanning type profiler creates two beams by a beam splitter as an imaging type does, the two beams either travel on same optical path, or have side-by-side paths. As a result, vibration effects are reduced. Due to its scanning nature, a scanning type profiler is limited in measurement speed.

Imaging and scanning type profilers have quite different structures. It is difficult to integrate the two into one setup to save cost. Therefore both profilers are needed for circumstances requiring a fast profile survey and less vibration sensitivity.

Accordingly, current interferometric optical profilers based on interference of amplitude-division suffer from difficulties of integrating imaging and scanning type profilers into one arrangement.

Optical coherence tomography (OCT) is an imaging technology capable of measuring three-dimensional structures of highly scattering media, such as a variety of biological tissues. It has great potentials in biomedical applications. An OCT system employs a low-coherence light source which emits a beam with a relatively short coherence length. Currently at the heart of OCT is an amplitude division interferometer, usually a Michelson interferometer. Like the above discussed interferometers used for an optical profiler, an OCT system splits a beam into two beams by a beam splitter. One beam propagates to a reference surface along a reference optical path, and the other beam to a sample medium along a sample optical path. The beams reflected by the reference surface and the sample medium are then recombined by the beam splitter.

Due to the nature of low coherence, the combined beams interfere with each other only when their optical path length difference is within the beam coherence length. The interference intensity and pattern contrast reach a maximum when the two optical path lengths are matched. For highly scattering sample media, various sample paths yield different optical path lengths, depending upon where a beam is reflected inside the media. Since a reference optical path length can be adjusted to match a sample optical path length, tuning the reference path length results in interference between the reference beam and a sample beam which is reflected from a layer at a depth inside the media. The interference intensity and patterns are related to the layer's optical properties, such as refractive index, birefringence, scattering coefficient, etc. A beam coherence length determines measurement resolution along the beam propagation direction. The shorter the coherence length is, the higher the measurement resolution. By combing the low coherence interference technique with a laterally scanning mechanism, a three-dimensional image can be constructed.

Since the reference and sample optical paths are separate, they might experience different environmental changes. Thus the optical path length difference is sensitive to environmental variations, so does the interferometric measurement. The setup is also bulky due to the two separate paths.

Accordingly, the current OCT system based on interference of amplitude-division suffers from sensitivity to environmental variations and a bulky structure.

Besides biomedical applications, the OCT technology also has advantages in multi-layer optical data storage. Multi-layer optical storage media, which contain a three-dimensional distribution of reflectors, resemble highly scattering media, and can be detected by an OCT system. But the current OCT measurement is sensitive to sample vibration due to two separate optical paths, and it is difficult to apply the technology to read out data on a rotating optical disc.

Multi-layer optical storage media have been proposed with OCT readout methods. See, for example, U.S. Pat. No. 5,883,875 (1999) to Coufal, et al. and U.S. Pat. No. 6,072,765 (2000) to Rolland, et al. As a result, the multi-layer media only contain storage layers and not a reference reflector. The reflector is usually integrated with the OCT optical structure. Since readout results depend upon an optical path length to a storage layer, any vibration causes a change of the optical path length and brings measurement errors.

Accordingly, a multi-layer optical data storage device has difficulties in utilizing current OCT technology, and readout results of current multi-layer optical storage media are sensitive to vibration.

Like above discussions, most interferometric devices in use today are amplitude-division types. However, wavefront division interferometers are also known. For example, Bhagavatula describes an interferometric filter containing a spatial phase modulator in U.S. Pat. No. 5,841,583 (1998). The spatial phase modulator divides a beam into two portions by wavefront-division and creates a phase difference between them. The two portions have side-by-side optical paths. Interference of the portions occurs without generating two separate optical paths in different directions. An interferometric optical device which uses wavefront division is simpler and more compact than one that uses amplitude division, thanks to its optical path feature. However, the interferometric filter is mainly for light wave processing. Its ability to interact with surrounding media is limited besides detecting a refractive index along its beam path.

OBJECTS AND ADVANTAGES

Accordingly, several main objects and advantages of the present invention are:

a). to provide an improved interferometric optical device;

b). to provide such a device which divides a beam into two portions by wavefront-division and creates a phase difference between the two portions;

c). to provide such a device as an interferometric optical profiler which utilizes the beam portions to measure a surface profile;

d). to provide such a device which integrates imaging and scanning types of interferometric optical profilers;

e). to provide such a device as an OCT system which is relatively simple, compact, and insensitive to environmental variations;

f). to provide such a device which utilizes the beam portions to read out a multi-layer optical storage medium and is insensitive to vibration; and g). to provide a multi-layer optical storage medium comprising both storage and reference layers.

Further objects and advantages will become apparent from a consideration of the drawings and ensuing description.

SUMMARY

In accordance with the present invention, an interferometric optical device is constructed. The optical device divides a beam into two beam portions by wavefront division and performs phase retardation on each portion. The two beam portions with adjustable phase difference are then used for an interferometric optical profiler, an OCT system, or an optical data storage system.

For example, when the beam portions impinge upon a sample surface, they interact with different areas of the surface. Combining the reflected beam portions results in interference which is related to the surface profile. Since the beam portions have side-by-side optical paths, the interference result is relatively less sensitive to vibration and environmental variations than that with two separate optical paths.

If the two beam portions impinge upon a sample and a reference surface respectively, superposition of the beam portions results in an interference pattern containing topography information of a sample surface area.

In OCT applications, because the beam portions have side-by-side optical paths until they are close to a sample medium or an objective, the effect of environmental variations is reduced. The OCT structure is also more compact than one that has to accommodate two separate optical paths.

The OCT technology can also be used to read out a multi-layer optical storage medium. The beam portions have side-by-side optical paths and the multi-layer medium comprises at least one reference layer. Thus effect of vibration is reduced.

ABBREVIATIONS

AR Anti-reflection
HR High Reflection
OCT Optical Coherence Tomography
PR Partial Reflection

DRAWING FIGURES

FIG. 1 is a schematic diagram showing a prior-art spatial phase modulator processing a beam.

FIGS. 2-A to 2-C are schematic diagrams illustrating embodiments to measure a sample surface by using two beam portions according to the invention.

FIG. 3 is a schematic diagram illustrating an embodiment of a scanning type profiler or an OCT system according to the invention.

FIG. 4 is a schematic diagram illustrating an embodiment of an imaging type profiler according to the invention.

FIGS. 5-A and B are schematic diagrams illustrating embodiments of a scanning type profiler or an OCT system according to the invention.

FIG. 6 is a schematic diagram illustrating an embodiment to integrate scanning and imaging type profilers according to the invention.

FIGS. 7-A and B are schematic diagrams illustrating methods to change an optical path length mechanically.

FIG. 7-C is a schematic diagram showing a beam being divided into four portions.

FIGS. 8-A to 8-C are schematic diagrams illustrating embodiments of profilers and OCT systems with a relatively simple structure according to the invention.

Figure 9:
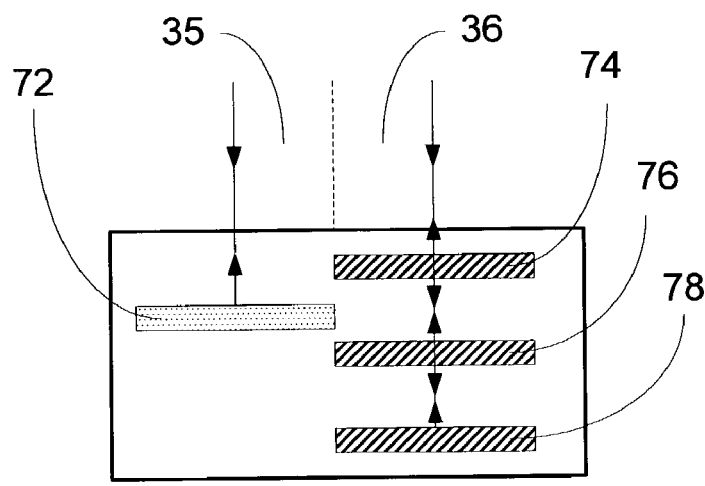

FIG. 9 is a schematic cross-sectional view illustrating an embodiment of a multi-layer optical data storage arrangement according to the invention.

Figure 10:
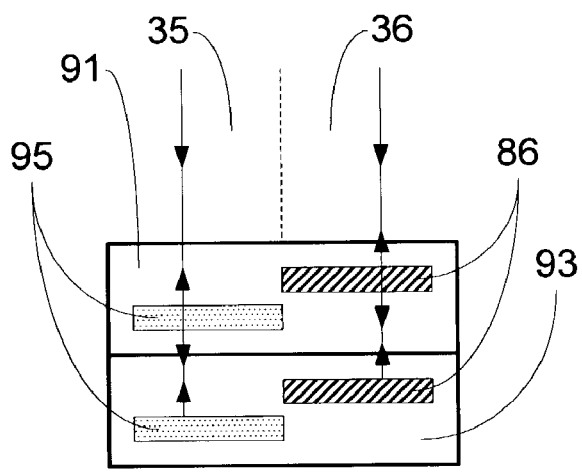
Figure 11:
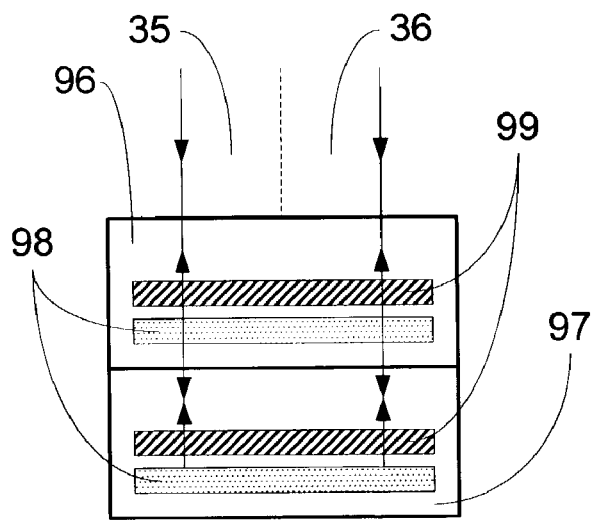

FIGS. 10 and 11 are schematic cross-sectional views illustrating embodiments of a multi-disc optical data storage arrangement according to the invention.

REFERENCE NUMERALS IN DRAWINGS

| 12 | collimated beam | 14 | modulator element |
|---|---|---|---|
| 16 | modulator element | 17 | spatial phase modulator |
| 18 | beam portion | 20 | beam portion |
| 21 | sample | 22 | sample |
| 23 | sample surface | 26 | HR reflector |
| 27 | PR reflector | 30 | lens system |
| 31 | modulator element | 32 | sample surface |
| 33 | AR coating | 34 | sample surface |
| 35 | beam portion | 36 | beam portion |
| 37 | spatial phase modulator | 38 | spatial phase modulator |
| 40 | lens system | 42 | single-mode fiber |
| 44 | fiberoptic coupler | 46 | single-mode fiber |
| 48 | single-mode fiber | 49 | PR coating |
| 50 | detector | 51 | detector |
| 52 | lens system | 54 | beam splitter |
| 56 | beam splitter | 58 | lens system |
| 61 | beam portion | 62 | beam portion |
| 63 | detector | 64 | beam portion |
| 65 | beam portion | 66 | HR reflector |
| 67 | AR coating | 68 | HR reflector |
| 69 | AR coating | 70 | retro-reflector |
| 71 | light source | 72 | reflective reference layer |
| 73 | AR coating | 74 | PR storage layer |
| 75 | HR coating | 76 | PR storage layer |
| 77 | modulator element | 78 | PR storage layer |
| 79 | sample | 80 | beam portion |
| 82 | beam portion | 84 | beam portion |
| 85 | beam portion | 86 | PR storage layer |

-continued

| 91 | optical disc | 93 | optical disc |
| 94 | lens system | 95 | PR reference layer |
| 96 | optical disc | 97 | optical disc |
| 98 | PR reference layer | 99 | PR storage layer |

DETAILED DESCRIPTION

FIG. 1—Prior-Art Spatial Phase Modulator

FIG. 1 shows schematically a prior-art spatial phase modulator 17 processing a collimated beam 12. Spatial phase modulator 17 contains modulator elements 14 and 16, which divide beam 12 into two beam portions by wavefront division. Elements 14 and 16 have anti-reflection (AR) coatings (not shown in FIG.1) on their surfaces to reduce power loss and avoid unwanted interference due to reflection.

Besides dividing the beam, the spatial phase modulator also creates a phase difference between the beam portions. Usually a phase difference is generated by elements with different refractive indexes, or elements with same refractive index but different physical dimensions along a beam propagation direction.

If elements 14 and 16 contain electro-optical materials, for example, liquid crystal or lithium niobate, a phase difference between beam portions 18 and 20 can be tuned electro-optically. Other methods to tune the phase difference include rotating one modulator element to change an optical path length. For example in FIG. 1, the rotating axis is perpendicular to an interface of the elements. Rotating element 14 around the rotating axis changes phase retardation of beam portion 18.

FIGS. 2-A–2-C—Using Two Beam Portions to Measure a Surface

FIG. 2-A illustrates schematically an embodiment of the invention which utilizes two beam portions with a phase difference in a surface profile measurement. A sample 22 has an uniform index of refraction and two surfaces 32 and 34. Beam portions 18 and 20, which have a phase difference created by a spatial phase modulator (not shown in FIG. 2-A), impinge onto surfaces 32 and 34, respectively. Since surfaces 32 and 34 are not leveled, they affect the optical path length of a reflected beam differently. In other words, surface reflection changes the phase difference between the impinging beam portions. The reflected beam portions now contain information of both the modulator and the surface in terms of a final phase difference. By adjusting the spatial phase modulator to generate different interference patterns, a step between surfaces 32 and 34 can be calculated. A profiler based on the scheme of FIG. 2-A measures a step between two spots on a surface each time. Thus a profile is constructed if the profiler scans continually from one spot to its adjacent spot on the surface.

In cases of low-coherence light source, interference occurs only when an optical path length difference between the portions is within the beam coherence length, and interference intensity and contrast are maximized when the beam portions have matching optical path lengths. The portions are created from a collimated beam, thus matching optical path lengths mean that the spatial phase modulator compensates change of phase difference caused by surfaces 32 and 34. Since the phase difference caused by the modulator is known, a step between surface 32 and 34 can be obtained.

Beam portions 18 and 20 in FIG. 2-A have side-by-side optical paths; thus vibration of sample 22 has limited effects on a phase difference of the beam portions.

FIG. 2-B illustrates schematically another embodiment of the invention which utilizes two beam portions with a phase difference in a surface profile measurement. The system of FIG. 2-B is similar to that of FIG. 2-A, except that a high reflection (HR) reflector 26 is added to reflect beam portion 18. Phase difference of the reflected beam portions now depends upon the following factors: (1) a spatial phase modulator (not shown in FIG. 2-B), (2) the position of reflector 26, which is controllable, (3) distance between reflector 26 and surface 34, and (4) the profile of surface 34. As in FIG. 2-A, the reflected beam portions are combined to generate interference. Tuning the spatial phase modulator results in different interference patterns which in turn lead to profile information of surface 34. The method detects one spot at a time. The resulting profiler is of the scanning type.

If the light source is of low coherence, the setup can also be used as an OCT system. Assume that sample 22 is a highly scattering medium. When beam portion 20 impinges onto sample 22, the reflected light contains a mixture of reflection, not only from the surface, but also from inside of the medium. Due to the nature of low-coherence interference, an interference phenomena can be obtained which is related to one layer of sample 22, where the layer makes the reflected beam portion 20 have an matched optical path length to that of reflected beam portion 18. Thus optical information at a depth can be acquired by tuning the spatial phase modulator.

FIG. 2-C illustrates schematically another embodiment which utilizes two beam portions with a phase difference in a surface profile measurement. Again beam portions 18 and 20 have a phase difference created by a spatial phase modulator (not shown in FIG. 2-C). A partial reflection (PR) reflector 27 reflects beam portion 18, while portion 20 is focused by a lens system 30 and impinges onto a surface 23 of a sample 21. Bean portion 20 is then reflected by surface 23 and collimated by lens system 30. Due to reflection on surface 23, part of the reflected portion 20 transmits through reflector 27 and superposes reflected portion 18.

Since reflector 27 is partially reflective, part of portion 18 passes through it, impinges onto surface 23, and then is reflected back by surface 23. The reflected portion 18 then passes through reflector 27 and superposes the other part of portion 18, which is reflected by reflector 27. For the same reason, part of the reflected portion 20 is reflected back to surface 23 by reflector 27, and then is reflected by surface 23 again. So the superposition of portion 18 and 20 contains at least two pairs of beam portions which can have matched optical path lengths. The first pair has one reflection for each beam portion. The second pair involves three reflections for portion 18, including double reflections from surface 23. For the second pair, both the optical paths contain one route: reflector 27 to surface 23 to reflector 27. In case of a reflective surface 23, let portion 18 contains non-central part of the beam. Then it impinges onto surface 23 with an incident angle and surface 23 reflects portion 18 to places other than reflector 27. In this way, the second pair of optical paths and other optical paths involving multiple reflections can be ignored, since these paths have heavy optical power losses.

The modulator, position of reflector 27, the distance between reflector 27 and surface 23, and the surface area where portion 20 impinges determine an interference pattern between the reflected portions 18 and 20. Tuning the modulator results in different interference patterns and a surface profile can be obtained from that. The profiler is of imaging type, and is preferred for use on a reflective surface.

FIGS. 3 and 4—Profilers and OCT Systems

FIG. 3 shows schematically an embodiment of an optical profiler which utilizes two beam portions with a phase difference according to the invention. The embodiment is based on the configuration illustrated in FIG. 2-A. First collimated beam 12 enters spatial phase modulator 17 and becomes beam portions 18 and 20 with a phase difference. Then beam portions 18 and 20 pass through a beam splitter 54 and are focused onto surface 23 of sample 21 by lens system 30. The two beam portions impinge on different part of the surface and are reflected back to lens system 30. The reflected beam portions are then reflected by beam splitter 54 and are focused onto detector 50 by a lens system 52. What detector 50 measures is interference intensity of beam portions 18 and 20. As discussed in FIG. 2-A, this scanning type profiler measures relative position between two surface spots each time and is vibration-insensitive. If the light source has low coherence, the configuration in FIG. 3 can be used as an OCT system for multi-layer optical data storage, which will be discussed later.

FIG. 4 depicts schematically another embodiment of an optical profiler which utilizes two beam portions with a phase difference. The embodiment results from the setup in FIG. 2-C. As in FIG. 2-C we consider cases where surface 23 is reflective, and ignore optical paths involving routes from reflector 27 to surface 23 then back to reflector 27. Here spatial phase modulator 17 processes collimated beam 12 and generates beam portions 18 and 20. Portion 18 impinges onto surface 23 and gets reflected by the surface, while portion 20 passes through a beam splitter 56 and is reflected by PR reflector 27. As discussed in FIG. 2-C, the two reflected portions superpose each other. The superposed beam portions are reflected by a beam splitter 56, processed by a lens system 58, and reach a detector 51. To measure an interference pattern, detector 51 contains a photodiode array. In FIG. 4, modulator 17 can also be disposed between beam splitter 56 and reflector 27.

FIGS. 5-A and 5-B—Profilers and OCT Systems

FIG. 5-A shows schematically another embodiment of an optical profiler which utilizes two beam portions with a phase difference as that in FIG. 2-B. Spatial phase modulator 17 divides collimated beam 12 to produce beam portions 18 and 20. Portion 18 passes through beam splitter 54 and is focused onto surface 23 by lens system 30. Surface 23 reflects portion 18, and the reflected portion 18 is collimated by lens system 30. Meanwhile, portion 20 passes through beam splitter 54 and is reflected by HR reflector 26. Both reflected portions 18 and 20 are then reflected by beam splitter 54 and are focused onto detector 50 by lens system 52. Detector 50 measures interference intensity of the two beam portions. Each time one spot on the surface is measured. The device is a scanning type profiler. Modulator 17 can also be placed between beam splitter 54 and reflector 26, which makes beam portions 18 and 20 go through the modulator twice.

Due to the need to combine the reflected portions 18 and 20, beam 12 should be divided such that an adequate amount of portion 18 is reflected back along its incident path. One way is to let portion 18 have the central part of the beam.

FIG. 5-B illustrates schematically another embodiment of an optical profiler which is a modification of the setup in FIG. 5-A. Here a beam is coupled into a single-mode fiber 48 from a light source (not shown in FIG. 5-B). A 1×2 fiberoptic coupler 44 couples fiber 48 with another single-mode fiber 46, which leads to a detector (not shown in FIG. 5-B). On the other side of coupler 44 is a single-mode fiber 42. A beam emerging from fiber 42 is processed to form collimated beam 12 by a lens system 40. Beam 12 then enters a spatial phase modulator 37 which produces beam portions 18 and 20. As in FIG. 5-A, surface 23 and reflector 26 reflect portions 18 and 20, respectively. The reflected portions then re-enter modulator 37 and are coupled into fiber 42 by lens system 40. The two reflected beam portions interfere with each other when they propagate along fiber 42. Then the reflected light waves are split into two waves by coupler 44 and one wave propagates along fiber 46 to reach the detector.

The embodiment in FIG. 5-B makes it possible to place a light source and a detector in another location away from the sample, which makes the setup flexible and is often desired in many applications.

With a low-coherence light source, the embodiments in FIGS. 5-A and 5-B can be used as an OCT system. The resulting OCT is simpler and smaller than the current OCT which has to accommodate two separate optical paths. Due to the side-by-side optical paths up to reflector 26, the environment affects a smaller part of the OCT system comparing to the current OCT configurations. If there are two separate optical paths, the two paths occupy a relatively large space and might experience different environmental variations, which in turn causes changes of optical path length difference and measurement errors. Especially if the two optical paths are along two optical fibers, the movement or bending of a fiber affects the optical intensity and polarization states, and causes additional errors. However in FIG. 5-B, the effects of optical fiber are cancelled since both waves experience the same changes.

FIG. 6—Integration of Scanning and Imaging Type Profilers

To integrate scanning and imaging type profilers, an embodiment is shown schematically in FIG. 6. The embodiment combines the schemes of FIGS. 3 and 4. A spatial phase modulator (not shown in FIG. 6) creates and modulates beam portions 18 and 20 and works for the scanning type profiler, along with beam splitter 54, lens system 52, and detector 50. Another spatial phase modulator 38 works for the imaging type profiler, and so does beam splitter 56, lens system 58, and detector 51. Modulator 38 has only one modulator element and is aligned to beam portion 20 to adjust its phase retardation. Modulator 38 has an AR coating 33 on its front surface and a PR coating 49 on its rear surface. Due to the existence of two beam portions and two reflectors, which are surface 23 and PR coating 49, multi-wave interference occurs. For example, beam portion 18 alone has many paths to detector 50 due to two modulators, two reflectors, and reflection between the reflectors. Therefore I prefer a low-coherence light source such that a detector can pick up interference signals only among waves whose optical path length difference is within the beam coherence length.

For the scanning type profiler, there are two pairs of paths which can have matched optical path lengths simultaneously. Each pair contains two paths for beam portions 18 and 20 to reach detector 50. For the first pair, each beam portion goes through modulator 38 once and is reflected by surface 23 once. For the second pair, portion 18 is reflected by surface 23 once and doesn't enter modulator 38, while portion 20 is reflected by PR coating 49, goes through modulator 38 twice, and doesn't impinge onto surface 23. Since adjusting modulator 38 only affects light path difference of the second pair, modulator 38 can be used to make the path length difference of the second pair too large for interfere to happen.

The imaging type profiler in FIG. 6 works similarly as in FIG. 4, except that two modulators instead of one adjust phase retardation of the beam portions. As in FIG. 4, the profiler is preferred to use on a reflective surface.

FIGS. 7-A–7-C—Spatial Phase Modulators

A mechanically tuned spatial phase modulator is depicted schematically in FIG. 7-A. A retro-reflector 70 and two HR reflectors 66 and 68 are disposed to modulate the phase difference between beam portions 64 and 62. Reflector 66 is aligned to reflect portion 64 only. The reflected beam portion enters retro-reflector 70, then is reflected by reflector 68 to join portion 62 in a side-by-side position. The phase difference can be tuned by moving retro-reflector 70.

Another mechanically tuned spatial phase modulator is depicted schematically in FIG. 7-B. The modulator adjusts phase of one beam portion only. Moving a reflector 68 tunes the optical path length of a reflected beam portion 64. It can be used to replace HR reflector 26, and modulators 17 and 37 in FIGS. 5-A and 5-B, for example.

FIG. 7-C shows schematically that a beam is divided into four portions, 80, 82, 84, and 85. A beam with four portions with respective phase retardation can be used as a tool to measure a surface. For a scanning type profiler, four beam portions can increase measurement speed. For example, by using one portion as a reference to interfere with the other beam portions, three spots can be measured at each scanning position. Since four portions introduce a possible four-wave interference, a low-coherence light source is preferred. By using features of low-coherence interference and a spatial phase modulator (not shown in FIG. 7-C), interference between any two portions can be obtained.

FIGS. 8-A–8-C—Profilers and OCT Systems with a Relatively Simple Structure FIGS. 8-A to 8-C depict schematically several embodiments of profilers which have a simpler structure than that discussed above. In FIG. 8-A, a light source 71 with a light-emitting point (not shown in FIG. 8-A) is placed adjacent to a detector 63. Two modulator elements 77 and 31 form a spatial phase modulator. Element 31 works mainly as a protective shield. The two elements divide a beam emitted by light source 71 into two portions, 61 and 65. Element 77 has two surfaces coated with an AR coating 73 and a HR coating 75 respectively. Portion 61 enters element 77 and is reflected back by HR coating 75. Element 77 is designed with such a shape that coating 75 reflects beam portion 61 back to the light-emitting point with a uniform phase retardation over its wavefront. Element 31 has two surfaces coated with AR coatings 67 and 69. Beam portion 65 passes through element 31, encounters a sample 79, and is reflected by the sample surface. Element 31 is designed to give beam portion 65 a uniform phase retardation. Being reflected by sample 79, part of portion 65 converges to the light-emitting point.

The light-emitting point of light source 71 is placed close enough to a light-detecting point (not shown in FIG. 8-A) of detector 63 such that detector 63 detects interference between part of portions 61 and 65 which are reflected back to the source. HR coating 75 serves as a reference reflector. Element 77 may contain electro-optical materials to tune phase retardation of portion 61 electrically, or have a structure to adjust the phase retardation mechanically.

If sample 79 has a reflective surface, interference signals represent a value which is averaged over the measured surface area. If sample 79 is a highly scattering medium, the reflected portion 65 contains reflection from both surface and inside the medium. In such a case, a low-coherence optical source is needed to turn the setup into an OCT system. For the system, element 77 and HR coating 75 define a reference optical path length for beam portion 61. Interference signals reveal averaged information of one region of sample 79, which region generates a matching optical path length to the reference optical path length.

FIG. 8-B shows schematically a similar embodiment to FIG. 8-A with addition of fiberoptic coupler 44, and single-mode fibers 42, 46, and 48. As in FIG. 5-B, fiber 48 is coupled to a light source (not shown in FIG. 8-B) and fiber 46 is coupled to a detector (not shown in FIG. 8-B). A beam is emitted from or collected by an end of fiber 42. The embodiment enables flexible applications, since it make it possible to place a light source and a detector away from a phase modulator and a sample.

To increase the measurement distance for the schemes in FIGS. 8-A and 8-B, a lens system 94 is added to the setup as shown schematically in FIG. 8-C. Without the lens system, sample 79 has to be placed close to the elements so that the reflected signals have an adequate intensity. With a lens system, the sample can be away at a distance from the elements. The lens system can also be placed between light source 71 and the element.

FIGS. 9–11—Multi-Layer Optical Storage Structures

Reverting to FIG. 3, the profiler arrangement can be used as an OCT system with a low-coherence light source. Obviously the resulting OCT doesn't work for detecting a highly scattering medium due to lack of a controllable reference reflector. But in optical storage applications, the same OCT system finds use in sensing a multi-layer optical data storage medium, since a reference reflector can be planted adjacent a storage reflector inside the medium. Unlike current OCT systems, the OCT described in FIG. 3 is vibration-insensitive due to its side-by-side optical paths.

A schematic cross-sectional view in FIG. 9 illustrates an embodiment of structure and method for multi-layer optical data storage. The multi-layer optical storage medium contains two regions. A first region has a single PR or HR reference layer 72 as a reference reflector. A second region has PR storage layers 74, 76, and 78 as three storage reflectors with respective spacings in a direction perpendicular to the layers. Surrounding the reference and storage layers are low-loss transmissive materials. Stored data are represented by either a partial reflection or a relatively low reflection of the storage layer. Readout beam portions 35 and 36 are created and tuned by a spatial phase modulator (not shown in FIG. 9), and are aligned to the two regions respectively. Portion 35 impinges onto layer 72, and portion 36 impinges onto the three storage layers.

For portion 35, it has only one reference optical path involving one reflection from layer 72. But due to the three storage reflectors, beam portion 36 has three storage optical paths containing a single reflection, and various storage optical paths containing multiple reflections. One storage path of portion 36 has a route from the modulator to layer 74, to layer 76, to layer 74, to layer 76, to layer 74, and finally to a detector. By assigning respective values to spacings between the storage layers, where at least the spacing between the storage layers should be equal to or larger than half the beam coherent length divided by the refractive index, it is possible to make each storage path have a distinguishable optical path length. Tuning the spatial phase modulator can match the reference optical path length to any of the storage optical path lengths. Thus a low-coherence light source enables interference between portion 35 and only one part of portion 36 which has a matching optical path length.

For readout purpose, only three storage paths involving a single reflection are needed. By tuning the phase modulator to match the optical path lengths respectively, reflectivity of the three storage layers can be detected.

The medium structure in FIG. 9 can be applied to an optical disc. Unlike the current optical discs which either have a single-layer structure or multi-layer structure, the disc according to the embodiment has both single-layer and multi-layer sections. The single layer is the reference reflector, and the multi-layer carries stored multiple data.

A schematic cross-sectional view in FIG. 10 illustrates an embodiment of a multi-disc optical data storage configuration. Optical discs 91 and 93 contain a PR storage layer 86 and a PR reference layer 95. Surrounding the reference and storage layers are low-loss transmissive materials. The discs are stacked and their reference layers and storage layers are aligned in a direction perpendicular to the layers. Layer 95 functions as a reference reflector for an adjacent storage layer 86 in the same disc. Layer 86 stores information by its reflectivity value. The two discs are distinguished by different spacings between layers 86 and 95 in a direction perpendicular to the layers, and thickness of each disc is larger than the beam coherent length.

To read out data, two beam portions 35 and 36 impinge onto layers 95 and 86, respectively. Each beam portion impinges on two layers which are in separate discs. The spacing between layers 86 and 95 in each disc is known and it causes a specific optical path length difference between the reflected beam portions. Although there are two reflectors which cause multiple reference and storage optical paths, it is possible to make the optical path length difference a distinct value for a disc. Again as in FIG. 9, interference between beam portions 35 and 36, which are reflected by a reference layer and a storage layer in the same disc respectively, can be singled out as a tool to measure reflectivity of the storage layer.

FIG. 11 illustrates another embodiment of a multi-disc optical data storage configuration through a schematic cross-sectional view. In the embodiment, a PR storage layer 99 overlaps a PR reference layer 98 in discs 96 and 97. Surrounding the reference and storage layers are low-loss transmissive materials. The two discs are stacked together. Each of beam portions 35 and 36 impinges onto the four PR layers in two discs. Again the spacing between a reference layer and a storage layer in each disc is distinct, equal to or larger than half the beam coherence length divided by the refractive index, and is used to distinguish one disc from the other. Thickness of each disc is larger than the beam coherent length.

The overlapped layers mean that a reflected reference and storage beam portions can have same optical path length inside the storage medium. But the spatial phase modulator adds respective values to optical path lengths of a reference and sample beam portion, such that every optical path has a distinct path length. Therefore as in FIG. 9, a low-coherence interference method is used to single out specific interference between beam portions 35 and 36. The interference only involves part of the reflected portion 35, which is reflected by a reference layer in a disc, and part of the reflected portion 36, which is reflected by a storage layer in the same disc. The interference information reveals reflectivity of the storage layer.

CONCLUSION, RAMIFICATIONS, AND SCOPE

Accordingly, the reader will see that two beam portions, created by wavefront-division and having a tunable phase difference, can be used to measure topography as an optical profiler, to provide a profiler which integrates imaging and scanning types, to provide an OCT system with less environmental sensitivity and a relatively simple and compact structure, and to construct a multi-layer optical data storage system.

Although the description above contains many specificities, these should not be construed as limiting the scope of the invention but as merely providing illustrations of some of the presently preferred embodiments. Numerous modifications, alternations, and variations will be obvious to those skilled in the art. For example, a single disc containing multiple reference and storage layers can replace the multi-disc structures in FIG. 10 or 11. To replace the scheme in FIG. 9, multiple storage layers can be arranged in respective discs with a common reference reflector attached to them. A collimated beam can be produced either directly from a light source, or from a single-mode fiber which is coupled to the light source. A beam can be divided into portions of any number with any geometrical shapes by wavefront-division; for example, a beam can be divided into a central circular portion and several outer ring-shaped portions. The intensity ratio of one portion to another can be of any value depending upon the interference effect between them. In FIGS. 5-A and 5-B, for example, if surface 23 has low reflectivity, portion 18 should have a larger intensity than portion 20 to improve contrast of interference patterns. The scheme in FIG. 7-A can be modified by adding another set of two reflectors and one retro-reflector to process portion 62. The resulting modulator can tune the two beam portions simultaneously and is more flexible to use. As the schemes illustrate in FIGS. 8-A and 8-B, a spatial phase modulator can process any beam besides a collimated beam which is most often presented. Lastly in FIG. 10, the reference layers in two discs can be misaligned based on the schemes shown in FIG. 11.

Therefore the scope of the invention should be determined by the appended claims and their legal equivalents, rather than by the examples given.

The invention claimed is:

1. An interferometric optical device comprising:
   1) a light source for generating a beam;
   2) a spatial phase modulator for dividing said beam into a plurality of beam portions by wavefront division and producing phase shift on at least one of said beam portions;
   3) a plurality of media disposed to receive and return at least two of said beam portions including said phase shifted beam portion respectively; and
   4) a detector for sensing interference by said returned beam portions.

2. The optical device according to claim 1 wherein said media include a sample under test.

3. The optical device according to claim 2, further including scanning means and data processing means for obtaining an image of said sample.

4. The optical device according to claim 1, further including combining optics for combining said returned beam portions.

5. The optical device according to claim 1 wherein said combining optics includes first lens means for focusing said returned beam portions onto said detector.

6. The optical device according to claim 1, further including positioning means for controlling position of at least one of said media.

7. The optical device according to claim 1, further including second lens means for focusing at least one of said beam portions onto at least one of said media.

8. The optical device according to claim 1, further including third lens means for collimating said beam from said light source.

9. The optical device according to claim 1 wherein said detector includes a detector array.

10. The optical device according to claim 1 wherein said light source has relatively low coherence.

11. The optical device according to claim 1, further including a plurality of single-mode optical fibers which are coupled to said light source and said detector respectively.

12. The optical device according to claim 1, further including tuning means for adjusting said phase shift.

13. A method for generating optical interference, comprising:
   1) providing a light source for generating a beam;
   2) providing a spatial phase modulator for dividing said beam into a plurality of beam portions by wavefront division and phase shifting at least one of said beam portions;
   3) receiving and returning at least two of said beam portions including said phase shifted beam portion by at least one medium; and
   4) sensing interference by said returned beam portions through a detector.

14. The method according to claim 13, further including adjusting said phase shift.

15. The method according to claim 13, further including combining said returned beam portions.

16. An optical device for measuring a sample comprising:
   1) a light source for generating a beam;
   2) a spatial phase modulator for dividing said beam into a plurality of beam portions by wavefront division and producing phase shift on at least one of said beam portions;
   3) at least one medium, said medium and said sample being disposed for receiving and returning said beam portions including said phase shifted beam portion respectively; and
   4) a detector for sensing interference by said returned beam portions.

17. The device according to claim 16, further including lens optics for focusing at least one of said beam portions onto said sample.

18. The device according to claim 16 wherein said light source has relatively low coherence.

19. The device according to claim 16, further including tuning means for adjusting said phase shift.

20. A method for generating optical interference, comprising;
   1) causing a light source to generate a beam;
   2) providing a detector for sensing an optical output;
   3) providing at least one medium;
   4) dividing said beam into a plurality of beam portions by wavefront division by providing a spatial phase modulator and transmitting said beam portions through a plurality of optical paths from said source to said detector respectively, said optical paths each being arranged via at least one of said media;
   5) adjusting the optical path length of at least one of said optical paths; and
   6) sensing an interferometric optical output caused by said beam portions by said detector.

* * * * *